(12) United States Patent
Santonico

(10) Patent No.: US 10,302,652 B2
(45) Date of Patent: May 28, 2019

(54) HYBRID PROTEIN FOR THE IDENTIFICATION OF NEDDYLATED SUBSTRATES

(71) Applicant: Elena Santonico, Rome (IT)

(72) Inventor: Elena Santonico, Rome (IT)

(*) Notice: Subject to any disclaimer, the term of this patent is extended or adjusted under 35 U.S.C. 154(b) by 0 days.

(21) Appl. No.: 15/550,886

(22) PCT Filed: Feb. 16, 2016

(86) PCT No.: PCT/IT2016/000039
§ 371 (c)(1),
(2) Date: Aug. 14, 2017

(87) PCT Pub. No.: WO2016/132393
PCT Pub. Date: Aug. 25, 2016

(65) Prior Publication Data
US 2018/0074072 A1    Mar. 15, 2018

(30) Foreign Application Priority Data
Feb. 17, 2015  (IT) .............................. RM2015A0072

(51) Int. Cl.
| | |
|---|---|
| A61K 38/00 | (2006.01) |
| G01N 33/68 | (2006.01) |
| C07K 14/47 | (2006.01) |
| C12N 9/22 | (2006.01) |
| C12N 9/10 | (2006.01) |

(52) U.S. Cl.
CPC ......... *G01N 33/6848* (2013.01); *C07K 14/47* (2013.01); *C07K 14/4702* (2013.01); *C12N 9/1088* (2013.01); *C12N 9/22* (2013.01); *C12Y 205/01018* (2013.01); *C07K 2319/00* (2013.01); *C07K 2319/23* (2013.01); *C07K 2319/70* (2013.01); *G01N 2440/36* (2013.01); *G01N 2560/00* (2013.01)

(58) Field of Classification Search
None
See application file for complete search history.

(56) References Cited

U.S. PATENT DOCUMENTS

2014/0106981 A1* 4/2014 Hood .................. G01N 33/6845 506/9

OTHER PUBLICATIONS

International Search Report, dated Jul. 5, 2016, from corresponding PCT Application No. PCT/IT2016/000039.
Tanaka, T., Kawashima, H., Yeh, E. T., & Kamitani, T. (2003). Regulation of the NEDD8 conjugation system by a splicing variant, NUB1L. Journal of Biological Chemistry, 278(35), 32905-32913.
Anantharaman, V., & Aravind, L. (2006). The NYN domains: novel predicted RNAses with a PIN domain-like fold. RNA biology, 3(1), 18-27.
Database Geneseq [online] Aug. 19, 2002 (Aug. 19, 2002), "Human peptide encoded by genome-derived single exon probe SEQ ID 36172.", XP002740827, retrieved from EBI accession No. GSP:ABG46507 Database accession No. ABG46507.
Marco, A., & Marin, I. (2009). CGIN1: a retroviral contribution to mammalian genomes. Molecular biology and evolution, 26(10), 2167-2170.
Hori, T., Osaka, F., Chiba, T., Miyamoto, C., Okabayashi, K, Shimbara, N., ... & Tanaka, K. (1999). Covalent modification of all members of human Guilin family proteins by NEDD8. Oncogene, 18(48).
Duncan, K., Schafer, G., Vava, A., Parker, M. I., & Zerbini, L. F. (2012). Targeting neddylation in cancer therapy. Future Oncology, 8(11), 1461-1470.
Mori, F., Nishie, M., Piao, Y. S., Kito, K., Kamitani, T., Takahashi, H., & Wakabayashi, K. (2005). Accumulation of NEDD8 in neuronal and glial inclusions of neurodegenerative disorders. Neuropathology and applied neurobiology, 31(1), 53-61.
Kuazi, A. D., Kito, K., Abe, Y., Shin, R. W., Kamitani, T., & Ueda, N. (2003). NEDD8 protein is involved in ubiquitinated inclusion bodies. The Journal of pathology, 199(2), 259-266.
Choo, Y. S., Vogler, G., Wang, D., Kalvakuri, S., Iliuk, A., Tao, W. A., ... & Zhang, Z. (2012). Regulation of parkin and PINK1 by neddylation. Human molecular genetics, 21(11), 2514-2523.
Soucy, T. A., Smith, P. G., Milhollen, M. A., Berger, A. J., Gavin, J. M., Adhikari, S., ... & Cullis, C. A. (2009). An inhibitor of NEDD8-activating enzyme as a new approach to treat cancer. Nature, 458(7239), 732.
Tanaka, T., Nakatani, T., & Kamitani, T. (2012). Inhibition of NEDD8-conjugation pathway by novel molecules: potential approaches to anticancer therapy. Molecular oncology, 6(3), 267-275.
Hjerpe, R., Thomas, Y., & Kurz, T. (2012). NEDD8 overexpression results in neddylation of ubiquitin substrates by the ubiquitin pathway. Journal of molecular biology, 421(1), 27-29.
Hjerpe, R., Thomas, Y., Chen, J., Zemla, A., Curran, S., Shpiro, N., ... & Kurz, T. (2012). Changes in the ratio of free NEDD8 to ubiquitin triggers NEDDylation by ubiquitin enzymes. Biochemical Journal, 441(3), 927-936.

(Continued)

*Primary Examiner* — Jeanette M Lieb
(74) *Attorney, Agent, or Firm* — Silvia Salvadori, P.C.; Silvia Salvadori

(57) ABSTRACT

Disclosed is a recombinant protein composed by the fusion of Glutathione S-transferase (GST), or an esa-histidine peptide (poly-His), or Maltose Binding Protein (MBP), to the Carboxyl-terminus end of the human KHNYN protein, containing residues 597-678 or a region including at least the amino acidic region 630-678. Also disclosed is a second recombinant protein where the Carboxyl-terminus end of the human KHNYN protein, containing residues 627-678 is genetically fused in a tandem construct to the Carboxyl-terminus end of KHNYN including residues 597-678. The tandem construct is N-terminally tagged with Glutathione S-transferase (GST), or an esa-histidine peptide (poly-His), or Maltose Binding Protein (MBP). The potential use of these "Neddylation sensors" also called "Neddylation probes" to isolate mono-, poly-neddylated targets as well as substrates modified by the addition of ubiquitin-NEDD8 mixed chains is considered.

6 Claims, 3 Drawing Sheets
Specification includes a Sequence Listing.

(56) References Cited

OTHER PUBLICATIONS

Xirodimas, D. P., Saville, M. K., Bourdon, J. C., Hay, R. T., & Lane, D. P. (2004). Mdm2-mediated NEDD8 conjugation of p53 inhibits its transcriptional activity. Cell, 118(1), 83-97.

Watson, I. R., Blanch, A., Lin, D. C., Ohh, M., & Irwin, M. S. (2006). Mdm2-mediated NEDD8 modification of TAp73 regulates its transactivation function. Journal of Biological Chemistry, 281(45), 34096-34103.

Oyed, S., Mosesson, Y., Zwang, Y., Santonico, E., Shtiegman, K., Marmor, M. D., . . . & Yarden, Y. (2006). Conjugation to Nedd8 instigates ubiquitylation and down-regulation of activated receptor tyrosine kinases. Journal of Biological Chemistry, 281(31), 21640-21651.

Ikeda, F., Crosetto, N., & Dikic, I. (2010). What determines the specificity and outcomes of ubiquitin signaling?. Cell, 143(5), 677-681.

Schmidtke, G., Kalveram, B., Weber, E., Bochtler, P., Lukasiak, S., Hipp, M. S., & Groettrup, M. (2006). The UBA domains of NUB1L are required for binding but not for accelerated degradation of the ubiquitin-like modifier FAT10. Journal of Biological Chemistry, 281(29), 20045-20054.

Whitby, F. G., Xia, G., Pickart, C. M., & Hill, C. P. (1998). Crystal structure of the human ubiquitin-like protein NEDD8 and interactions with ubiquitin pathway enzymes. Journal of Biological Chemistry, 273(52), 34983-34991.

Chew, E. H., Poobalasingam, T., Hawkey, C. J., & Hagen, T. (2007). Characterization of cullin-based E3 ubiquitin ligases intact mammalian cells—evidence for cullin dimerization. Cellular signalling, 19(5), 1071-1080.

\* cited by examiner

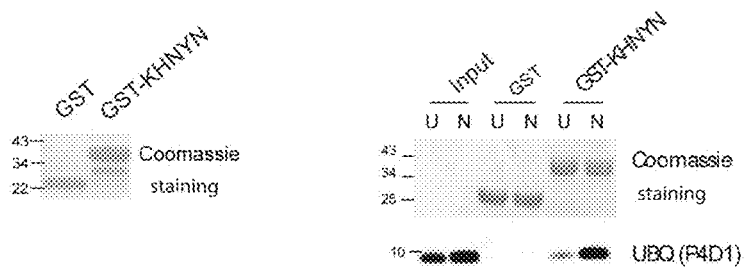
Fig. 1
Fig. 2
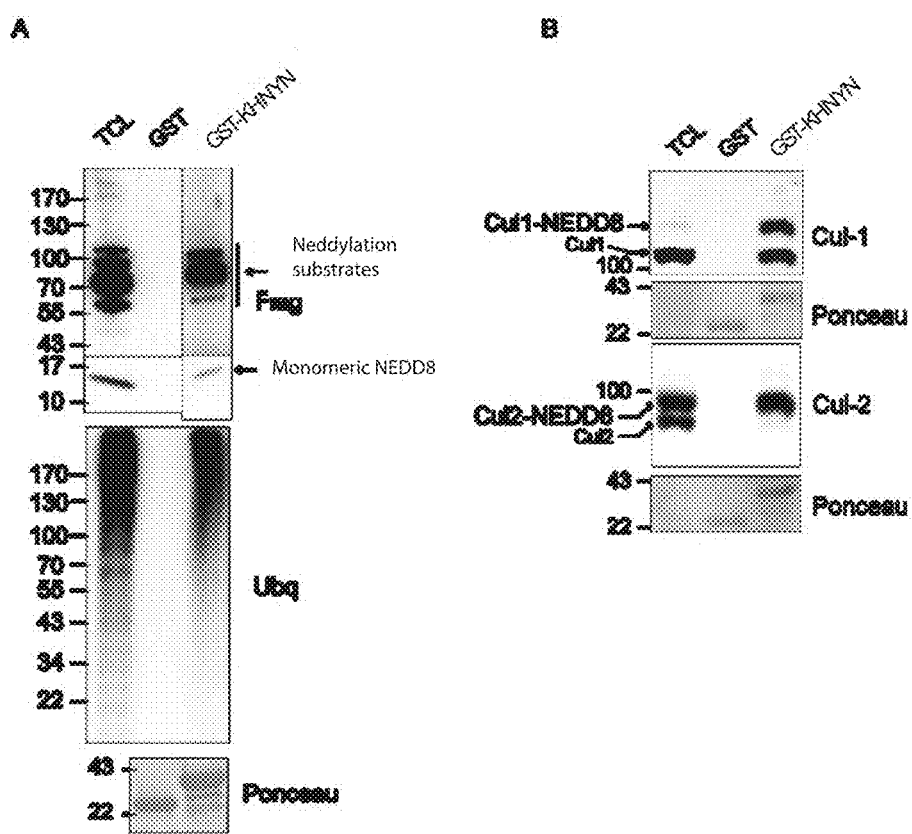
Fig. 3

SEQUENCE LISTING

```
<160> NUMBER OF SEQ ID NOS: 9

<210> SEQ ID NO 1
<211> LENGTH: 249
<212> TYPE: DNA
<213> ORGANISM: Homo Sapiens

<400> SEQUENCE: 1
acacaggggt cttctaaggc tcagcatcct tccaggggct ttgcagaaca tggtaaacag      60
cagcagggga gagaagagga aaaaggtagt ggtggcattc ggaagacccg ggaaacagag     120
cggctccggc ggcagctgct ggaggtgttt tggggtcagg atcacaaagt ggacttcatc     180
ctgcagcggg agccatactg ccgggacatc aaccaactgt ctgaggccct gctcagtctt     240
aacttttga                                                            249

<210> SEQ ID NO 2
<211> LENGTH: 82
<212> TYPE: PRT
<213> ORGANISM: Homo Sapiens

<400> SEQUENCE: 2

Thr Gln Gly Ser Ser Lys Ala Gln His Pro Ser Arg Gly Phe Ala Glu
1               5                   10                  15

His Gly Lys Gln Gln Gln Gly Arg Glu Glu Glu Lys Gly Ser Gly Gly
            20                  25                  30

Ile Arg Lys Thr Arg Glu Thr Glu Arg Leu Arg Arg Gln Leu Leu Glu
        35                  40                  45

Val Phe Trp Gly Gln Asp His Lys Val Asp Phe Ile Leu Gln Arg Glu
    50                  55                  60

Pro Tyr Cys Arg Asp Ile Asn Gln Leu Ser Glu Ala Leu Leu Ser Leu
65                  70                  75                  80

Asn Phe

<210> SEQ ID NO 3
<211> LENGTH: 405
<212> TYPE: DNA
<213> ORGANISM: Artificial sequence
<220> FEATURE:
<223> OTHER INFORMATION: Tandem repeat

<400> SEQUENCE: 3
ggtggcattc ggaagacccg ggaaacagag cggctccggc ggcagctgct ggaggtgttt      60
tggggtcagg atcacaaagt ggacttcatc ctgcagcggg agccatactg ccgggacatc     120
aaccaactgt ctgaggccct gctcagtctt aactttacac aggggtcttc taaggctcag     180
```

```
catccttcca ggggctttgc agaacatggt aaacagcagc aggggagaga agaggaaaaa      240
ggtagtggtg gcattcggaa gacccgggaa acagagcggc tccggcggca gctgctggag      300
gtgttttggg gtcaggatca caaagtggac ttcatcctgc agcgggagcc atactgccgg      360
gacatcaacc aactgtctga ggccctgctc agtcttaact tttga                     405
```

<210> SEQ ID NO 4
<211> LENGTH: 134
<212> TYPE: PRT
<213> ORGANISM: Artificial sequence
<220> FEATURE:
<223> OTHER INFORMATION: tandem repeat

<400> SEQUENCE: 4

```
Gly Gly Ile Arg Lys Thr Arg Glu Thr Glu Arg Leu Arg Arg Gln Leu
1               5                   10                  15

Leu Glu Val Phe Trp Gly Gln Asp His Lys Val Asp Phe Ile Leu Gln
            20                  25                  30

Arg Glu Pro Tyr Cys Arg Asp Ile Asn Gln Leu Ser Glu Ala Leu Leu
        35                  40                  45

Ser Leu Asn Phe Thr Gln Gly Ser Ser Lys Ala Gln His Pro Ser Arg
    50                  55                  60

Gly Phe Ala Glu His Gly Lys Gln Gln Gln Gly Arg Glu Glu Glu Lys
65                  70                  75                  80

Gly Ser Gly Gly Ile Arg Lys Thr Arg Glu Thr Glu Arg Leu Arg Arg
                85                  90                  95

Gln Leu Leu Glu Val Phe Trp Gly Gln Asp His Lys Val Asp Phe Ile
            100                 105                 110

Leu Gln Arg Glu Pro Tyr Cys Arg Asp Ile Asn Gln Leu Ser Glu Ala
        115                 120                 125

Leu Leu Ser Leu Asn Phe
    130
```

<210> SEQ ID NO 5
<211> LENGTH: 699
<212> TYPE: DNA
<213> ORGANISM: Artificial sequence
<220> FEATURE:
<223> OTHER INFORMATION: Nucleotide sequence of the Glutathione
      S-transferase used in pGex vectors

<400> SEQUENCE: 5

```
atgtcccta tactaggtta ttggaaaatt aagggccttg tgcaacccac tcgacttctt      60
ttggaatatc ttgaagaaaa atatgaagag catttgtatg agcgcgatga aggtgataaa      120
tggcgaaaca aaaagtttga attgggtttg gagtttccca atcttcctta ttatattgat      180
ggtgatgtta aattaacaca gtctatggcc atcatacgtt atatagctga caagcacaac      240
atgttgggtg gttgtccaaa agagcgtgca gagatttcaa tgcttgaagg agcggttttg      300
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg gatgcgttcc caaaattagt tgttttaaa       540 aaacgtattg aagctatccc acaaattgat aagtacttga atccagcaa gtatatagca       600 tggcctttgc agggctggca agccacgttt ggtggtggcg accatcctcc aaaatcggat      660
```
ctggttccgc gtggatctcg tcgtgcatct gttggatcc                                699

<210> SEQ ID NO 6
<211> LENGTH: 948
<212> TYPE: DNA
<213> ORGANISM: Artificial sequence
<220> FEATURE:
<223> OTHER INFORMATION: Genetic fusion of the GST with the C-terminal
      end of KIAA0323

<400> SEQUENCE: 6 atgtcccta tactaggtta ttggaaaatt aagggccttg tgcaacccac tcgacttctt    60
ttgaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctggttccgc gtggatctcg tcgtgcatct gttggatcca cacagggtc ttctaaggct   720
cagcatcctt ccagggggctt tgcagaacat ggtaaacagc agcaggggag agaagaggaa   780
aaaggtagtg gtggcattcg gaagacccgg gaaacagagc ggctccggcg gcagctgctg   840
gaggtgtttt ggggtcagga tcacaaagtg gacttcatcc tgcagcggga gccatactgc   900
cgggacatca accaactgtc tgaggccctg ctcagtctta acttttga                948

<210> SEQ ID NO 7
<211> LENGTH: 315
<212> TYPE: PRT
<213> ORGANISM: Artificial sequence
<220> FEATURE:
<223> OTHER INFORMATION: Genetic fusion of the GST with the C-terminal
      end of KIAA0323

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Arg Arg Ala Ser Val Gly Ser Thr Gln Gly Ser Ser Lys Ala
225                 230                 235                 240

Gln His Pro Ser Arg Gly Phe Ala Glu His Gly Lys Gln Gln Gln Gly
                245                 250                 255

Arg Glu Glu Glu Lys Gly Ser Gly Gly Ile Arg Lys Thr Arg Glu Thr
            260                 265                 270

Glu Arg Leu Arg Arg Gln Leu Leu Glu Val Phe Trp Gly Gln Asp His
        275                 280                 285

Lys Val Asp Phe Ile Leu Gln Arg Glu Pro Tyr Cys Arg Asp Ile Asn
    290                 295                 300

Gln Leu Ser Glu Ala Leu Leu Ser Leu Asn Phe
305                 310                 315

<210> SEQ ID NO 8
<211> LENGTH: 1110
<212> TYPE: DNA
<213> ORGANISM: Artificial sequence
<220> FEATURE:
<223> OTHER INFORMATION: Genetic fusion of the GST with the tandem
      repeat

<400> SEQUENCE: 8 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca tcttccttta ttatattgat    180
ggtgatgtta aattaacaca gtctatggcc atcatacgtt atatagctga caagcacaac    240
atgttgggtg ttgtccaaa agagcgtgca gagatttcaa tgcttgaagg gcggttttg      300 gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatctcg tcgtgcatct gttggatccg gtggcattcg aagaccccgg    720
gaaacagagc ggctccggcg gcagctgctg gaggtgtttt ggggtcagga tcacaaagtg    780
gacttcatcc tgcagcggga gccatactgc cgggacatca accaactgtc tgaggccctg    840
ctcagtctta actttagatc cacgcagggg tcttctaagg ctcagcatcc ttccaggggc    900
tttgcagaac atggtaaaca gcagcagggg agagaagagg aaaaaggtag tggtggcatt    960
```

```
cggaagaccc gggaaacaga gcggctccgg cggcagctgc tggaggtgtt ttggggtcag    1020
gatcacaaag tggacttcat cctgcagcgg gagccatact gccgggacat caaccaactg    1080
tctgaggccc tgctcagtct taacttttga                                     1110
```

<210> SEQ ID NO 9
<211> LENGTH: 369
<212> TYPE: PRT
<213> ORGANISM: Artificial sequence
<220> FEATURE:
<223> OTHER INFORMATION: Genetic fusion of the GST with the tandem repeat

<400> SEQUENCE: 9

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Arg Arg Ala Ser Val Gly Ser Gly Ile Arg Lys Thr Arg
225                 230                 235                 240

Glu Thr Glu Arg Leu Arg Arg Gln Leu Leu Glu Val Phe Trp Gly Gln
                245                 250                 255

Asp His Lys Val Asp Phe Ile Leu Gln Arg Glu Pro Tyr Cys Arg Asp
            260                 265                 270

Ile Asn Gln Leu Ser Glu Ala Leu Leu Ser Leu Asn Phe Arg Ser Thr
        275                 280                 285

Gln Gly Ser Ser Lys Ala Gln His Pro Ser Arg Gly Phe Ala Glu His
    290                 295                 300

Gly Lys Gln Gln Gln Gly Arg Glu Glu Lys Gly Ser Gly Gly Ile
305                 310                 315                 320

Arg Lys Thr Arg Glu Thr Glu Arg Leu Arg Arg Gln Leu Leu Glu Val
```

-continued

```
                325                 330                 335
Phe Trp Gly Gln Asp His Lys Val Asp Phe Ile Leu Gln Arg Glu Pro
                340                 345                 350
Tyr Cys Arg Asp Ile Asn Gln Leu Ser Glu Ala Leu Leu Ser Leu Asn
            355                 360                 365
Phe
```

HYBRID PROTEIN FOR THE IDENTIFICATION OF NEDDYLATED SUBSTRATES

FIELD OF THE INVENTION

The present invention proposes a method for the identification, at physiological conditions, of proteins subjected to mono-neddylation, poly-neddylation and modified by the addition of ubiquitin-NEDD8 mixed chains. The method can be applied to the analysis of cell lines, tissues or any other biological sample also eventually collected by patients. Moreover, it allows the characterization of samples at steady state or following any kind of treatment, whether chemical or biological, which can in principle, induces a modification in the neddylation pattern of known substrates as well as induce the neddylation of previously undescribed substrates.

TECHNOLOGICAL CONTEXT

Ubiquitination is a post-translation modification represented by the addition of a ubiquitin molecule to a substrate protein through the formation of a covalent bond. Analogously to ubiquitin, a broad family of proteins with ubiquitin-like activity can be conjugated to specific substrates. While ubiquitination affects a wide range of cellular proteins, several studies demonstrate that substrates modified by the addition of ubiquitin-like molecules represent only a small group. Among the ubiquitin-like molecules, NEDD8 shares with ubiquitin the higher sequence identity (58%), including the residues that are typically involved in the recognition by ubiquitin binding domains (UBD). To date, cullins represent the main class of proteins that are known to be targeted by neddylation [1]. Neddylation of cullins is a post-translation modification that is essential for the E3-ligase activity of Cullin-RING ubiquitin ligases (CRLs). These complexes regulate the turnover of substrates acting a key role in the control of cell cycle, inflammatory processes, replication, DNA repair and response to oxidative stress. It is not therefore surprising that the deregulation of cullin neddylation is involved in crucial steps of tumorigenesis [2]. Moreover, recent experimental evidences demonstrate that deregulation of neddylation is also responsible for the etiology of several neurodegenerative diseases [3]. Inclusions positive for NEDD8 have been identified in a variety of intra-cytoplasmatic aggregates such as Lewis body in Parkinson disease (PD), Rosenthal fibers in the polycystic astrocytoma and the intranuclear inclusions in polyglutamine expansion diseases [4]. Accordingly, the involvement of NEDD8 in neurodegenerative diseases has been confirmed by the evidence that Parkin and PINK1 proteins are conjugated to NEDD8 and that loss of neddylation on Parkin and PINK1 contributes to Parkinson's pathogenesis [5]. The growing interest in biological functions regulated by neddylation has lead in recent years to the development of inhibitors, that selectively target the neddylation process and that in some cases have found application as treatment approach in cancer therapy and in neurodegenerative diseases. In this respect, the selective inhibitor MLN4924 has been demonstrated to be particularly effective, since it shows a substantial activity towards a broad spectrum of pre-clinical tumor models and acts exclusively on CRL E3 ligases, without altering the ubiquitination of substrates that are modified throughout the enzymatic activity of E3-ligases not belonging to the CRL type. Conversely, other inhibitors aimed at reducing the degradation of ubiquitinated substrates through the inhibition of the 26S proteasome activity (such as bortezomid or inhibitors that are currently under development as MLN9708, carfilzomib or CEP-18770), although proving effective in cancer therapies, they cause adverse health effects due to the numerous cellular processes that neddylation regulates, not least the appearance of non physiological neddylation substrates generated by "atypical" neddylation events. These atypical substrates have been shown to be insensitive to treatment with MLN4924, thus compromising therapy effectiveness [6,7]. Besides the development of selective inhibitors of the neddylation pathway, lines of research aiming at investigating the specificity of the neddylation process, as well as the biological mechanisms guaranteeing the discrimination between the NEDD8 and ubiquitin molecules, have been undertaken. To date, strategies applied for the identification of neddylation substrates have made use of NEDD8 molecules that are exogenously expressed in eukaryotic cells fused to a tag, typically a short sequence like 6xHis, Flag, HA or Myc. The poly-His tag allows the purification of NEDD8 substrates also in denaturing conditions, thus inactivating NEDD8 specific proteases and excluding the co-purification of non covalent NEDD8 interactors. Nevertheless, endogenous proteins containing histidine stretches are co-purified during the purification protocol. On the other hand, epitopes like HA, Flag and Myc allow the efficient purification of NEDD8 substrates but are not compatible with the complete protein sample denaturation. Consequently, the co-purification of non-covalently modified interactors cannot be excluded. Moreover, it has been demonstrated that NEDD8 overexpression, even though at low levels, induces the atypical neddylation of endogenous proteins, thus calling for a degree of caution in interpreting results. The use of proteasome inhibitors, such as MG132, that induces the depletion of intracellular ubiquitin levels, has an analogous effect [8,9]. Finally, using antibodies directed against endogenous NEDD8, although available, has not proved effective given the low affinity and the high degree of sequence conservation between NEDD8 and ubiquitin molecules. Accordingly, a large part of the neddylated substrates other than cullins, identified by several groups by proteomic approaches, have not been confirmed by subsequent studies [10-12]. Thus, it will be of great importance to generate the neddylome under unchallenged conditions as well as after exposure to standard chemotherapeutic agents both in non-cancer and cancer cells. The characterization of the neddylome will permit the identification of biomarkers for the prediction of specific diseases or resistance to current therapies. Recently, the research in the ubiquitin field has benefited from the use of ubiquitin binding domains to generate sensors, also called probes, for the purification of endogenous ubiquitin [13]. Analogously, the identification or the engineering of probes that specifically recognize NEDD8 could provide an alternative and more advantageous approach for investigating biological processes governed by neddylation. However, to date a protein domain that selectively recognizes NEDD8 in the monomeric form as well as covalently conjugated to substrates has not been identified. Vice versa, a mounting body of evidence suggests a certain promiscuity between the mechanisms involved in the recognition of ubiquitin and NEDD8 molecules, as clearly demonstrated by the evidence that several binding domains recognizing ubiquitin can also bind NEDD8 [14]. Accordingly, the observation that the hydrophobic patch centered on Ile44 in ubiquitin, that is responsible for most of the interactions with ubiquitin binding domains, is perfectly conserved in NEDD8 is consistent with the observed promiscuity [15].

SCOPE OF THE INVENTION

On the basis of the above considerations, there is need for developing a method for the identification of neddylated substrates, in an efficient and reproducible manner, avoiding at the same time those experimental conditions that are responsible for the generation of atypically neddylated substrates. The present invention relates to the use of an amino acid region, identified in the human KH and NYN domain containing protein (KHNYN) protein, which shows a clear preference for the ubiquitin-like NEDD8. KHNYN protein has been predicted to contain an N-terminal evolutionary conserved KH domain (K Homology), that is present in a wide variety of nucleic acid-binding proteins where it binds RNA and can function in RNA recognition, followed by the NYN domain (N4BP1, YacP Nucleases) spanning residues 435-600 with predicted ribonuclease activity, which is found in the eukaryotic proteins typified by the Nedd4-binding protein 1 and the bacterial YacP-like proteins. The region showing the ubiquitin and NEDD8 binding properties has been identified at the very Carboxyl-terminal end of KHNYN protein immediately downstream to the NYN domain and spanning residues 597-678. This region can be engineered with the aim of improving both the affinity and specificity of the recognition. The same region can be also repeated in tandem up to 4 repetitions, to improve the avidity as well as the binding efficiency toward mixed or single-type chains. The functional properties of the NEDD8 binding region, that we will call neddylation probe or neddylation sensor, have been deduced by several experimental evidences and can be summarized with the following statements: (1) the NEDD8 probe shows a clear preference for NEDD8 monomers compared to ubiquitin; (2) the NEDD8 sensor binds neddylated substrates expressed at physiological levels, in particular proteins belonging to the Cullins protein family can be pulled down in their neddylated form; (3) the NEDD8 sensor binds poly-neddylated substrates and can be used for isolating ubiquitin/NEDD8 mixed chains covalently attached to proteins; (4) the NEDD8 probe binds ubiquitinated substrates; (5) the recognition of neddylated substrates is in principle independent of the interaction with ubiquitinated substrates. The method here described consists of three steps: the first step is a pull-down assay performed by using the GST fusion of the C-terminal end of KHNYN as a "bait" to capture neddylated and ubiquitinated substrates; this step can be also performed using a Tandem construct named GST-Tandem, where the C-terminal end of KHNYN is duplicated in tandem; in the second step proteins that have been precipitated in the pull-down experiment with GST-KHNYN and GST-Tandem are treated with the Ubiquitin carboxyl-terminal hydrolase 8 (USP8) to remove ubiquitinated substrates. The third step requires the identification of neddylated substrates bound to GST-KHNYN and GST-Tandem by mass-spectrometry analysis.

In the preferred embodiment here proposed, whose procedure is described in detail in the present invention, the first two steps are fully described while the third step is not described in the present invention.

1) First Step: Pull-Down Assay

Briefly, the NEDD8 probe genetically fused to the Glutathione S-transferase (GST) or to any other amino acid sequence allowing the expression and purification of the recombinant protein in a prokaryotic system, is used to isolate all the neddylated substrates, as well mono and poly-ubiquitinated proteins that are expressed at physiological levels in a biological sample. This sample can be generated starting from a tissue or a cellular culture. By using a sufficient amount of GST fusion (that can be experimentally determined), it is possible to isolate both ubiquitinated and neddylated substrates, even when expressed at very low levels, as well as poly-neddylated substrates and substrates modified by ubiquitin-NEDD8 mixed chains. Accordingly, we expect that a neddylation sensor could also allow the isolation of proteins already known to be targeted by neddylation (i.e. cullins) but in a post-translational modification profile never described before.

2) Second Step: Removal of Ubiquitinated Substrates

Removal of ubiquitinated substrates from each sample is performed by incubating the glutathione beads with a de-ubiquitinating enzyme having a broad-spectrum recognition. In this way, conjugated monomeric ubiquitin as well as any topology of ubiquitin chains will be completely removed from the substrates associated to the GST fusion. The deubiquitinating enzymes USP2 and USP8 (Ubiquitin-specific-processing protease 2 and 8) are characterized by a broad-spectrum recognition and high in vitro activity, thus being equally useful for this purpose. After incubation, the de-ubiquitinating enzyme is removed by extensive washing together with ubiquitinated substrates that have undergone proteolitic cleavage. Treatment with de-ubiquitinating enzymes does not alter the association with neddylated substrates, provided that they are directly associated to the NEDD8 probe.

3) Third Step: Identification of Neddylated Substrates

Afterwards, neddylated substrates are identified by mass-spectrometry analysis and validated by western-blotting. The efficiency of this method lies on the advantages related to the procedure used to carry out each step of the protocol. First of all, the possibility to pack the NEDD8 probe at high density on an inert solid support showing a very low background (sepharose glutathione-beads) supports the isolation of substrates expressed at very low levels. Moreover, as demonstrated for sensors developed for the isolation of ubiquitinated substrates, we expect that the interaction of neddylated substrates with the NEDD8 probes will protect them from degradation, particularly in those cases where the modification is associated with higher instability of the substrate [13]. Finally, the high in vitro activity of the de-ubiquitinating enzymes guarantees the complete removal of un-neddylated substrates.

In the preferred embodiment here described, the approach proposed will permit to examine changes in the spectrum of neddylated substrates in different cellular conditions and genetic backgrounds. The development of NEDD8 probes, therefore, will allow the analysis of tissues and primary cell lines particularly in those cases where biological samples cannot be studied with traditional approaches. The NEDD8 probes could be a powerful tool for identifying tumor markers, potential diagnostic or therapeutic agents and novel approaches for treatment of several pathologies. In a possible alternative embodiment, the NEDD8 sensors can be used for identifying the subcellular localization of neddylated targets in live-cell imaging.

Description of the Recombinant Proteins GST-KHNYN and GST-Tandem

In the preferred embodiment described herein, the recombinant protein GST-KHNYN includes from the N-terminal to the C-terminal end: i) the glutathione S-transferase (GST) amino acid sequence and ii) the Carboxyl-terminus end of human KHNYN, including residues 597-678. The recombinant protein GST-Tandem includes from the N-terminal to the C-terminal end: i) the glutathione S-transferase (GST) amino acid sequence and ii) the amino acid region of human KHNYN spanning residues 627-678 and iii) the C-terminal end of KHNYN including residues 597-678. In the preferred embodiment, the recombinant protein GST-KHNYN is represented by the nucleotide and amino acid sequences respectively specified in SEQ ID No: 1 (DNA construct) and 2 (amino acid sequence). In the same embodiment, the recombinant protein GST-Tandem is represented by the nucleotide and amino acid sequences respectively specified in SEQ ID No: 3 (DNA construct) and 4 (amino acid sequence). Finally, the sequence of glutathione S-transferase is represented by the nucleotide sequence SEQ ID No: 5. The complete nucleotide and amino acid sequences of the recombinant protein GST-KHNYN are specified respectively in SEQ ID No: 6 (DNA construct) and 7 (amino acid sequence) while the complete nucleotide and amino acid sequences of the recombinant protein GST-Tandem are specified respectively in SEQ ID No: 8 (DNA construct) and 9 (amino acid sequence).

DETAILED DESCRIPTION OF THE INVENTION

In the following paragraph, the details for the development and use of the probes are described. Preferred embodiments can be performed following the three steps previously described or varying each step depending on the specific features of the expression system. Here is shown only one of the possible procedures. In the embodiment described in the present invention, the recombinant protein includes from the N-terminal to the C-terminal end: i) the glutathione S-transferase (GST) amino acid sequence; ii) a linker sequence localized downstream to the GST and iii) the Carboxyl-terminus end of human KHNYN. In the preferred embodiment, the GST fusion protein includes the nucleotide sequence coding for the C-terminal end of human KHNYN protein, spanning residues 597-678 and defined by the SEQ ID No.: 1, or an homologue having 60%, preferably at least 80%, most preferably at least 90% of sequence identity with SEQ ID No.: 1 and having the function of the native human KHNYN derived from SEQ ID: No.: 1; in the preferred embodiment, the GST fusion protein includes as a minimum the nucleotide sequence coding for the C-terminal end of human KHNYN protein, spanning residues 627-678 and defined by the SEQ ID No.: 1, or an homologue having 60%, preferably at least 80%, most preferably at least 90% of sequence identity with SEQ ID No.: 1 and having the function of the native human KHNYN derived from SEQ ID: No.: 1. In an alternative embodiment, analogously to what has been described for ubiquitin sensors, the minimal NEDD8 binding region of KHNYN spanning residues 627-678 can be repeated in tandem up to four repeats, eventually separated by a linker, with the aim of increasing the binding affinity for ubiquitinated and neddylated substrates.

If present, the linker is represented by an amino acidic chain of 1 to 20 aminoacids. The tandem repeat construct would allow the isolation of substrates that are modified by the addition of poly-neddylated chains as well as ubiquitin-NEDD8 mixed chains. In embodiments that are alternative to the one that is preferred and here described, the NEDD8 probe based on the KHNYN protein can be genetically fused to Maltose binding protein (MBP) or the esa-Histidine tag (6×His). In an alternative embodiment, which is not described here in detail, the NEDD8 sensor based on the human C-terminal end of KHNYN can be achieved through the genetically fusion of the Flag epitope, Myc epitope or any other amino acid sequence aimed at facilitating the expression and purification of the recombinant protein, following transient or stable transfection of the expression vector in eukaryotic cells.

Set out below is the description of the method used for the expression and purification of the recombinant proteins GST-KHNYN and GST-Tandem in prokaryotic cells. The amino acid region shows the features that guarantee the production of a highly soluble, abundant and stable protein. The recombinant construct comprehends the GST that is genetically fused to the NEDD8 binding region of KHNYN (GST-KHNYN) or the Tandem repeat (GST-Tandem). Probes construction follows the methods that are typically used in molecular biology, while the expression in bacterial cells and purification by affinity chromatography are used for the production of the recombinant protein.

Step I—Preparation of the Recombinant Proteins GST-KHNYN and GST-Tandem

The cDNA coding for the Carboxyl-terminus end (aa 597-678) of human KHNYN (SEQ ID No.: 1) has been amplified by PCR using as template a phagemid vector in which the indicated region is genetically fused to the C-terminal end of the capsid protein of lambda bacteriophage (1). For the amplification by PCR, the following primers have been used: R2249 (5' CAAGGATCCACGCAGGGGTCT-TCTAAG 3') adding a restriction site for the BamHI enzyme, and R2160 (5' GTTGAATTCTCAAAAGT-TAAGACTGAG 3' that inserts a restriction site for the EcoRI enzyme and the stop codon. The destination plasmid vector is pGex2TK from Pharmacia. The fragment obtained by PCR amplification has been digested with BamHI and EcoRI and ligated in the pGex plasmid vector, following the procedures described in Sambrook, Fritsch ET Maniatis "Molecular cloning, a laboratory manual" (1989). For the generation of the tandem construct, the amino acid region spanning residues 627-678 of human KHNYN was amplified by PCR using the following primers: the forward primer R2251 (5' CAAGGATCCGGTGGCATTCGGAAGACC 3') that introduces a restriction site for BamHI and the reverse primer R2150 (5' ACAGATCTGCAAAGTTAAGACT-GAGCAGGG 3') that inserts a restriction site for BglII and misses the stop codon. The purified DNA fragment was digested with BamHI and BglII and cloned in the GST-KHNYN plasmid previously linearized by BamHI digestion. The DNA extracted from isolated clones of GST-KHNYN and GST-Tandem was verified by nucleotide sequencing of the poly-linker.

Step II—Production and Purification of the Recombinant Proteins

The protocol for the expression and purification is derived from the standard protocol used for the production of proteins fused to the GST in bacterial cells. The procedure here specified for descriptive purpose can be varied in one or more steps.

Set out below is the description of the method used for the production of the recombinant protein GST-KHNYN and GST-Tandem. The plasmid coding for the Neddylation probes allows the expression in BL21 *E. coli* bacterial cells of the recombinant proteins under the control of IPTG (Isopropyl β-D-1-thiogalactopyranoside) inducible lac promoter. The protocol consists of three steps: (i) expression of the recombinant protein in BL21 cells; (ii) resuspension and solubilisation of the bacterial pellet and (iii) purification of the recombinant protein by affinity chromatography.

Step I: Induction of the Recombinant Protein in BL21 Bacterial Cells.

1. Transform the expression plasmid into BL21. Plate on antibiotic selection plates and incubate overnight at 37° C.

2. Resuspend a single colony in liquid culture with antibiotic (starter culture). Inoculate starter culture at a 1:100 dilution into expression media containing antibiotic.

3. Incubate at 37° C. with shaking until OD600 reaches 0.6-0.8.

4. Induce with 0.5 mM IPTG (Sigma, St. Louis, Mo.) and express protein for 5 hours at 30° C.

Step II: Resuspension and Solubilisation of the Bacterial Pellet

1. Centrifuge your bacterial culture for 20 minutes at 5,000 RPM.
2. Resuspend the bacterial pellet in 2 ml of lysis buffer prepared as follow:
   50 mM Tris pH 7.5, 100 mM NaCl, 2 mM EDTA, 2 mM DTT, 1 mM PMSF, 1% Triton, Protease inhibitor cocktail (Complete—SIGMA)
3. Freeze at −80° C.

Step III: Purification of the recombinant proteins GST-KHNYN and GST-Tandem by affinity chromatography.

1. Thaw the resuspended pellet and add fresh inhibitors.
2. Sonicate the suspension 5 times for 10 seconds (with 15 seconds pause between each pulse)
3. Centrifuge at 14,000 RPM for 20 minutes at 4° C.
4. Incubate the supernatant with 100 µl of glutathione-sepharose 4B (GE Healthcare) for 2 h at 4° C. Wash 5 times with 10 ml of lysis buffer.
5. Measure the protein concentration using the Bradford protein assay.
6. Check protein expression and purification by 10% SDS-PAGE followed by Coomassie blue staining (FIG. 1A,B).

The recombinant protein has a molecular weight of approximately 36 kDa for GST-linker-KHNYN and 45 kDa for the GST-Tandem construct.

Step III—Pull-Down Assay to Analyse the Binding Preference of KHNYN

To analyse the binding preference of KHNYN toward purified Ubiquitin and NEDD8, 25 µg of GST-KHNYN are incubated with 5 µg of purified Ubiquitin or NEDD8 monomers in PBS1× (137 mM NaCl, 2.7 mM KCl, 10 mM Na$_2$HPO$_4$, 1.8 mM KH$_2$PO$_4$) for 90 min at 4° C. After three washes with cold PBS1×, samples are analysed by Tricine-SDS-PAGE and immunoblotting with anti-Ubiquitin antibody from Santa Cruz (P4D1) that cross-reacts with NEDD8 and thus permits to recognize both monomers (FIG. 2). The result demonstrates that KHNYN shows a clear preference for NEDD8 monomers.

Step IV—Pull-Down Assay for the Isolation of Neddylated Substrates from a Cellular Extract To isolate neddylated proteins from a cell culture, a pull-down assay was performed by using as cellular model the 293 T-Rex-flag-NEDD8 cell line obtained by stable integration of human NEDD8 fused to the Flag epitope. After induction with Doxycycline for 18 hours, a set of bands migrating at different molecular weights can be revealed by western-blotting of the cellular extract with anti-Flag antibody, indicating that the Flag-tagged NEDD8 has been conjugated to several cellular proteins (FIG. 3A). In detail, cells grown on dish for 24 hours are incubated with doxycycline for the indicated times, then harvested and lysed in lysis buffer (25 mM Tris pH 7.5, 125 mM NaCl, 1% glycerol, 1 mM MgCl2, 1 mM orthovanadate, 1 mM PMSF, 10 mM NaF, 20 mM NEM, eukaryotic inhibitor cocktail, 0.5% Triton, 0.5% NP-40). Cellular extracts are incubated on ice for 20 minutes and then centrifuged at 13000 rpm for 20 min at 4° C. The supernatant is recovered and quantified by Bradford protein assay. A total amount of 2 mg of cellular extract is incubated with 50 µg of recombinant protein bound to glutathione-sepharose beads (GE Healthcare) for 2 hours in rotation at 4° C. Beads are washed three times with cold washing buffer (25 mM Tris pH 7.5, 125 mM NaCl, 1% glycerol, 1 mM MgCl2, 1 mM orthovanadate, 1 mM PMSF, 5 mM NaF, 5 mM NEM, eukaryotic inhibitor cocktail, 0.5% Triton, 0.5% NP-40) and resuspended in loading buffer (1% SDS, 10% glicerolo, 10 mM Tris-Cl, pH 6.8, 1 mM EDTA, 10 mM DTT, 0.05 mg/ml bromophenol blue). Samples are analysed by SDS-PAGE and immunoblotting with anti-Flag antibody (M2 monoclonal, SIGMA) and anti-ubiquitin (P4D1, Santa Cruz).

As shown in FIG. 3B, the Carboxyl-terminus end of KHNYN, but not the GST alone, precipitated neddylated proteins as well as monomeric NEDD8. The recombinant protein is also able to associate with ubiquitinated substrates as shown by the immunoblotting with anti-ubiquitin antibody. The same samples have been analysed with antibodies specific for CUL1 (Zymed) and CUL2 (Zymed) demonstrating that both proteins have been recovered by GST-KHNYN (FIG. 2B). Particularly, while CUL2 is recovered only in its neddylated form, CUL1 bound GST-KHNYN both in the neddylated and non-neddylated forms. This difference can be explained by the observation that neddylated CUL1 interacts with the un-modified form, thus generating a stable homodimer that is recovered by GST-KHNYN. On the contrary, CUL2 only dimerizes in the neddylated form [16].

Step V—In Vitro De-Ubiquitination and De-Neddylation Assays

Samples obtained by incubating the recombinant GST-KHNYN with a T-Rex flag-NEDD8 cellular extract are resuspended in 50 ml of cold PBS1× pre-mixed with 5 mg of purified human USP8. The reaction is incubated for 30 minutes at 30° C. After washing three times with PBS, the reaction is resuspended in loading buffer and analysed by SDS-PAGE and immunoblotting with anti-Flag and anti-ubiquitin as previously described (FIG. 4A). As shown, the complete loss of ubiquitinated substrates is demonstrated by the absence of any anti-Ubiquitin signal in the lane corresponding to USP8 enzyme treatment. To further confirm that the recognition by KHNYN requires the NEDD8 modification on cullins, T-Rex-flag-NEDD8 cells plated on dishes were incubated with the NEDD8-activating enzyme inhibitor MLN4924. The pull-down assay performed as previously described confirms that, in the absence of neddylation, CUL2 cannot be precipitated by the NEDD8 binding domain of KHNYN (FIG. 4B). Finally, we compared the interaction of KHNYN with ubiquitinated and neddylated substrates after treatment with the de-neddylating enzyme NEDP1, the de-ubiquitinating enzyme USP8 or the NEDD8-activating enzyme inhibitor MLN4924 (FIG. 4C). As shown, the interaction with flag-tagged cellular proteins is similarly disrupted after MLN4924 or NEDP1 treatments (lanes 5 and 6). The interaction with ubiquitinated substrates is partly affected by the removal of neddylated proteins (lane 6), suggesting that part of the ubiquitinated substrates recovered by pull-down are proteins that are associated to Cullin-based complexes or to other neddylated substrates.

Step VI—Isolation of Neddylated Substrates from a Deneddylation Defective Cell Line The interaction of the C-terminal end of KHNYN with neddylated substrates were analysed in a cellular system where specific experimental conditions leading to an inhibition of the deneddylation process have been adopted (deneddylation defective cell line, called DD). Compared to the wild-type cell line, a global increase of neddylation can be observed in DD cells (FIG. 5). Equal amounts of cellular extract obtained from both cell lines were used to perform a pull-down experiment with GST-KHNYN and GST alone. The result clearly shows that a consistent number of bands in the input lane are recovered in the pull-down with GST-KHNYN, clearly indicating that KHNYN can be, in fact, efficiently used as a NEDD8 probe for the isolation of different neddylated substrates. Moreover, by comparing the post-translation modification profiles of CUL1 and CUL2 in the input lanes, is clearly evident that the neddylation probe allowed the isolation of post-translationally modified isoforms of both cullins whose identity would be easily identified by western-blotting analysis. Finally, the binding efficiencies of GST-KHNYN and GST-Tandem toward neddylated substrates were compared in the pull-down assay shown in FIG. 6, which demonstrates that the Tandem construct shows higher avidity towards neddylated substrates compared to the GST-KHNYN recombinant protein. Therefore, the use of the C-terminal end of KHNYN as a neddylation probe, alone expressed as a tandem repeat, allows the isolation and subsequent identification by mass spectrometry analysis of mono-neddylated and poly-neddylated substrates as well as substrates modified by the addition of mixed ubiquitin-NEDD8 chains.

BRIEF DESCRIPTION OF FIGURES

FIG. 1. Equivalent quantities of GST, GST-KHNYN and GST-Tandem were analysed on 10% SDS-PAGE and visualized by coomassie blue staining.

FIG. 2. The recombinant construct GST-KHNYN shows a clear preference for NEDD8. Equal amounts of GST and GST-KHNYN were incubated with 5 mg of purified Ubiquitin or NEDD8 monomers in PBS1× (137 mM NaCl, 2.7 mM KCl, 10 mM $Na_2HPO_4$, 1.8 mM $KH_2PO_4$) for 90 min at 4° C. After three washes with cold PBS1×, samples were analysed by SDS-PAGE and immunoblotting with anti-Ubiquitin antibody from Santa Cruz (P4D1).

FIG. 3. (A,B) The recombinant protein GST-KHNYN bound neddylated proteins expressed at physiological levels in the inducible stable cell line T-Rex-flag-NEDD8. Equivalent quantities of GST and GST-KHNYN were incubated with 2 mg of cellular extract and the precipitated protein were analysed by SDS-PAGE together with 2% of the total cell lysate (20 mg) representing the input lane (total cell lysate, TCL). Immunoblotting with anti-Flag, anti-ubiquitin, anti-CUL1 and anti-CUL2 antibodies were performed as previously described. Filters were incubated with secondary antibodies conjugated to horseradish peroxidase (HRP). Chemiluminescence reaction derived from the incubation with the enzymatic substrate (Thermo Scientific Pierce) was acquired with the ImageQuant LAS 3000 Dark Box (GE Healthcare). The Ponceau staining confirmed that equal amounts of GST and GST-KHNYN were used.

BIBLIOGRAPHY

Figure 4:
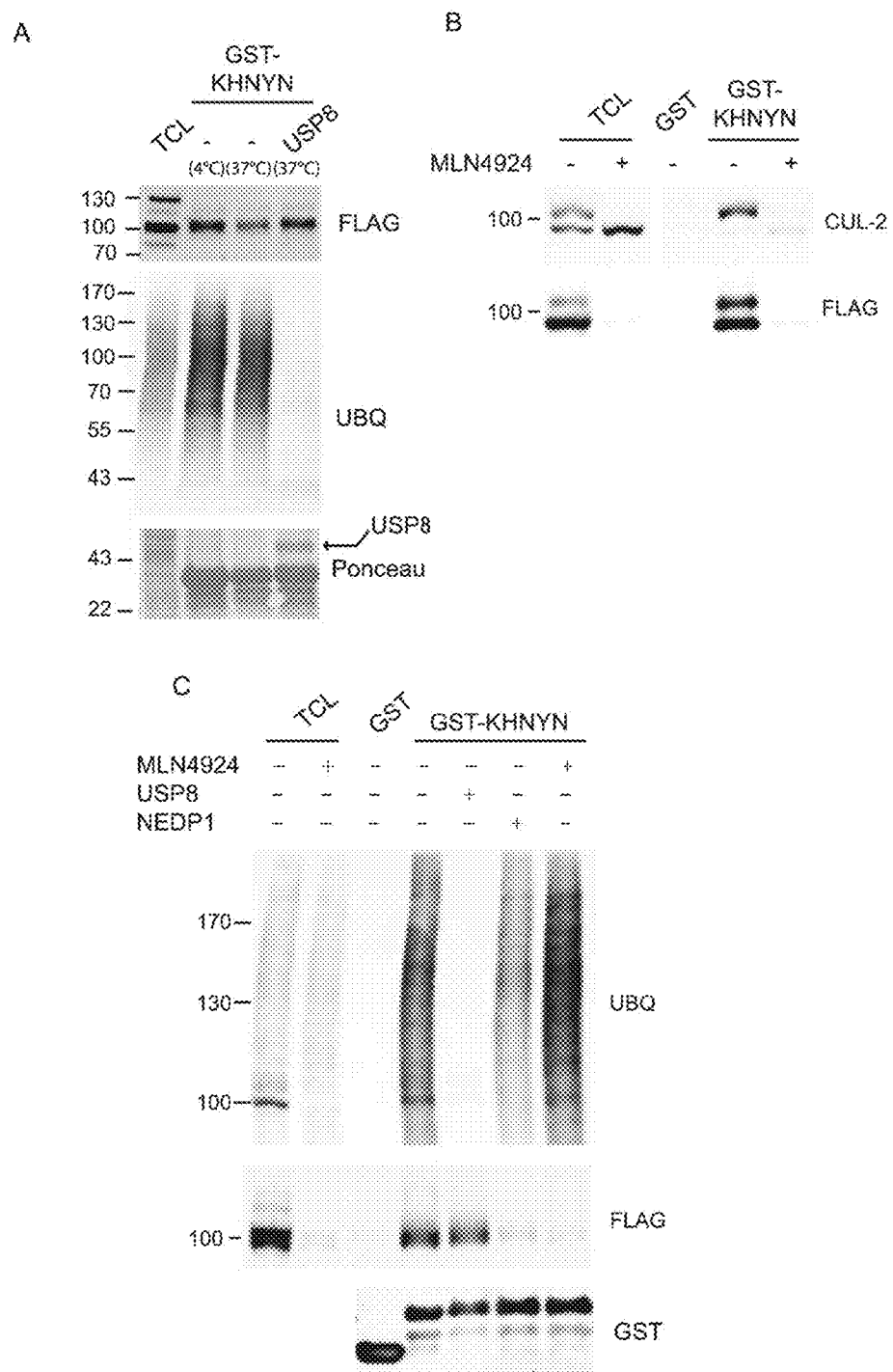
FIG. 4. (A) USP8 treatment removed the ubiquitinated substrates bound to GST-KHNYN without interfering in the interaction with neddylated substrates, thus excluding the involvement of ubiquitin in the recognition of neddylated substrates. The pull-down experiment previously described in FIG. 2 was sub-divided in three identical fractions that were incubated at 4° C., or at 37° C. with or without USP8 for 30 minutes. Samples were washed three times with PBS, resuspended in loading buffer and analysed by SDS-PAGE and immunoblotting with anti-Flag and anti-ubiquitin antibodies. (B) T-Rex-Flag-NEDD8 cells were incubated with MLN4924 uM for 3 h, the lysed and the cell extracts incubated with GST alone or GST-KHNYN. Bound proteins recovered after washing were analysed by western-blotting with anti-CUL2 and anti-Flag antibodies. (3) The pull-down was performed as previously shown in FIGS. 3A and 3B. Treatment with the de-ubiquitinating enzyme USP8 was performed by incubating washed beads, recovered after the pull-down assay, with 2 ug of purified enzyme for 30 min at 30° C.; treatment with the de-neddylating enzyme NEDP1 was performed by incubating the washed beads, recovered after the pull-down assay, with 2 ug of purified enzyme for 90 min at 30° C. Samples were analysed by SDS-PAGE and western-blotting with the indicated antibodies.
Figures 5, 6:
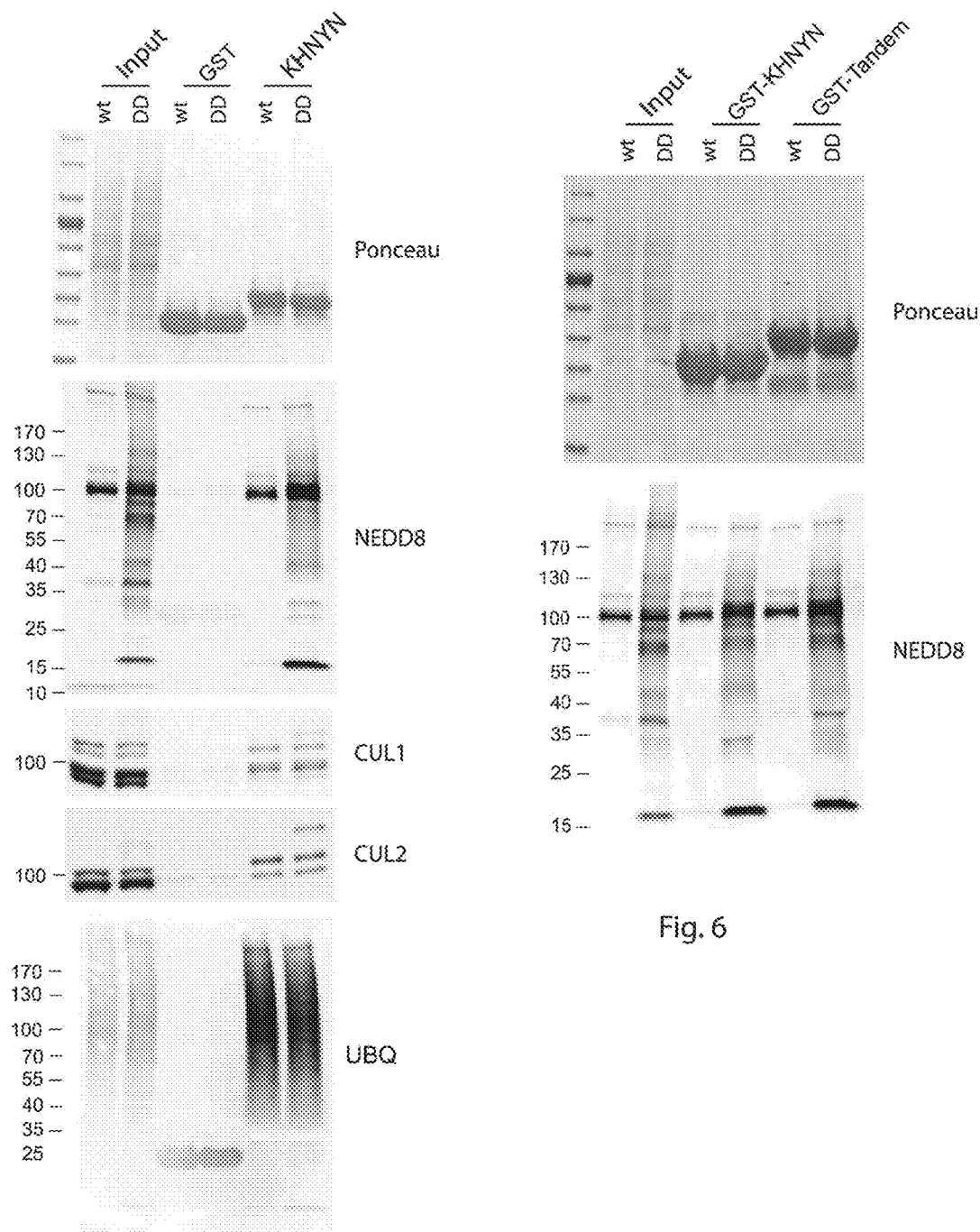
FIG. 5. KHNYN binds neddylated substrates from a deneddylation defective (DD) cell line. Wild type and DD cells were lysed and the cell extracts used to perform a pull-down assay as previously shown. Bound proteins were analysed by SDS-PAGE and immunoblotting with anti-NEDD8 antibody (Abcam), anti-Ubiquitin (Santa Cruz, P4D1) anti-CUL1 (Zymed) and anti-CUL2 (Zymed).
FIG. 6. The recombinant proteins GST-KHNYN and GST-Tandem were used to perform a pull-down assay aimed at comparing the binding efficiency towards neddylated substrates isolated from wild-type or deneddylation defective cells. Beads recovered after washing were analysed by SDS-PAGE and immunoblotting with anti-NEDD8 antibody (Abcam).

1. Hori, T., F. Osaka, et al. (1999). Covalent modification of all members of human cullin family proteins by NEDD8. Oncogene 18(48): 6829-6834.
2. Duncan K, Schafer G, Vava A, Parker M I, Zerbini L F. Targeting neddylation in cancer therapy. Future Oncol. 2012 November; 8(11):1461-70. doi: 10.2217/fon.12.131. Review.
3. Mori F, Nishie M, Piao Y S, Kito K, Kamitani T, Takahashi H, Wakabayashi K. Accumulation of NEDD8 in neuronal and glial inclusions of neurodegenerative disorders. Neuropathol Appl Neurobiol. 2005 February; 31(1):53-61.
4. Dil Kuazi A, Kito K, Abe Y, Shin R W, Kamitani T, Ueda N. NEDD8 protein is involved in ubiquitinated inclusion bodies. J Pathol 2003; 199(2):259-266.
5. Choo Y S, Vogler G, Wang D, Kalvakuri S, Iliuk A, Tao W A, Bodmer R, Zhang Z. Regulation of parkin and PINK1 by neddylation. Hum Mol Genet 2012; 21(11): 2514-2523.
6. Soucy T A, Smith P G, Milhollen M A, Berger A J, Gavin J M, Adhikari S, Brownell J E, Burke K E, Cardin D P, Critchley S, Cullis C A, Doucette A, Garnsey J J, Gaulin J L, Gershman R E, Lublinsky A R, McDonald A, Mizutani H, Narayanan U, Olhava E J, Peluso S, Rezaei M, Sintchak M D, Talreja T, Thomas M P, Traore T, Vyskocil S, Weatherhead G S, Yu J, Zhang J, Dick L R, Claiborne C F, Rolfe M, Bolen J B, Langston S P. An inhibitor of NEDD8-activating enzyme as a new approach to treat cancer. Nature. 2009 Apr. 9; 458(7239):732-6. doi: 10.1038/nature07884.
7. Inhibition of NEDD8-conjugation pathway by novel molecules: potential approaches to anticancer therapy. Tanaka T, Nakatani T, Kamitani T. Mol Oncol. 2012 June; 6(3):267-75. doi: 10.1016/j.molonc.2012.01.003. Epub 2012 Jan. 21. Review.
8. Hjerpe, R., Y. Thomas, et al. (2012). NEDD8 overexpression results in neddylation of ubiquitin substrates by the ubiquitin pathway. J Mol Biol 421(1): 27-29.
9. Hjerpe, R., Y. Thomas, et al. (2012). Changes in the ratio of free NEDD8 to ubiquitin triggers NEDDylation by ubiquitin enzymes. Biochem J 441(3): 927-936.

10. Xirodimas D P, Saville M K, Bourdon J C, Hay R T, Lane D P. Mdm2-mediated NEDD8 conjugation of p53 inhibits its transcriptional activity. Cell. 2004 Jul. 9; 118(1):83-97.
11. Watson I R, Blanch A, Lin D C, Ohh M, Irwin M S. Mdm2-mediated NEDD8 modification of TAp73 regulates its transactivation function. J Biol Chem. 2006 Nov. 10; 281(45):34096-103. Epub 2006 Sep. 14.
12. Oved S, Mosesson Y, Zwang Y, Santonico E, Shtiegman K, Marmor M D, Kochupurakkal B S, Katz M, Lavi S, Cesareni G, Yarden Y. Conjugation to Nedd8 instigates ubiquitylation and down-regulation of activated receptor tyrosine kinases. J Biol Chem. 2006 Aug. 4; 281(31): 21640-51. Epub 2006 May 30.
13. Ikeda F, Crosetto N, Dikic I. (2010). What determines the specificity and outcomes of ubiquitin signaling? Cell. 143(5):677-81. doi: 10.1016/j.cell.2010.10.026.
14. Schmidtke, G., B. Kalveram, et al. (2006). The UBA domains of NUB1L are required for binding but not for accelerated degradation of the ubiquitin-like modifier FAT10. J Biol Chem 281(29): 20045-20054.
15. Whitby, F. G., G. Xia, et al. (1998). Crystal structure of the human ubiquitin-like protein NEDD8 and interactions with ubiquitin pathway enzymes. J Biol Chem 273(52): 34983-34991.
16. Chew, E. H., T. Poobalasingam, et al. (2007). Characterization of cullin-based E3 ubiquitin ligases in intact mammalian cells—evidence for cullin dimerization. Cell Signal 19(5): 1071-1080.

The invention claimed is:

1. A recombinant fusion protein binding ubiquitinated and neddylated substrates expressed at physiological levels in a biological sample, said recombinant fusion protein comprising
an amino acid sequence selected from the group consisting of SEQ ID NO: 2, a sequence from amino acid 31 to 82 of SEQ ID NO: 2, a homologue with at least 60% sequence identity to SEQ ID NO: 2, and a homologue with at least 60% sequence identity to the sequence from amino acid 31 to 82 of SEQ ID NO: 2,
said amino acid sequence being genetically fused to an amino acid sequence of Glutathione S-transferase coded by SEQ ID NO:5 or to an amino acid sequence selected from group consisting of Maltose binding protein, esa-Histidine tag, human influenza hemagglutinin (HA) tag, the Flag epitope and the Myc epitope, wherein said amino acid sequence allows or facilitates expression and purification of said recombinant fusion protein,
wherein said recombinant fusion protein binding ubiquitinated and neddylated substrates expressed at physiological levels.

2. The fusion protein according to claim 1, wherein the amino acid sequence of SEQ ID NO: 2 and the sequence from amino acid 31 to 82 of SEQ ID NO: 2 are genetically fused to form a tandem repeat having the amino acid of SEQ ID NO: 4.

3. The fusion protein according to claim 1, having amino acid sequence of SEQ ID NO: 7 or of SEQ ID NO: 9.

4. A sensor or probe for the identification of biomarkers for cancer or neurodegenerative diseases, comprising the recombinant fusion protein according to claim 1.

5. A method for the identification of neddylated substrates in a biological sample comprising contacting such sample with the recombinant fusion protein according to claim 1.

6. The method according to claim 5 comprising the following steps:
a) contacting the sample with a recombinant fusion protein to capture neddylated and ubiquinated substrates, thus obtaining protein precipitates, said recombinant fusion protein binding ubiquitinated and neddylated substrates expressed at physiological levels in a biological sample and comprising an amino acid sequence selected from the group consisting of SEQ ID NO: 2, a sequence from amino acid 31 to 82 of SEQ ID NO: 2, a homologue with at least 60% sequence identity to SEQ ID NO: 2, and a homologue with at least 60% sequence identity to the sequence from amino acid 31 to 82 of SEQ ID NO: 2,
said amino acid sequence being genetically fused to an amino acid sequence of Glutathione S-transferase coded by SEQ ID NO:5 or to an amino acid sequence-selected from the group consisting of Maltose binding protein, esa-Histidine tag, human influenza hemagglutinin (HA) tag, the Flag epitope and the Myc epitope, wherein said amino acid sequence allows or facilitates expression and purification of said recombinant fusion protein,
wherein said recombinant fusion protein binding ubiquitinated and neddylated substrates expressed at physiological levels;
b) treating the protein precipitates obtained in step a) with Ubiquitin carboxyl-terminal hydrolase 8 (USP8) to remove ubiquinated substrates; and
c) identifying the neddylated substrates obtained in step b) by mass-spectroscopy analysis.

* * * * *